(12) United States Patent
Lin et al.

(10) Patent No.: US 12,710,414 B2
(45) Date of Patent: Aug. 18, 2026

(54) SYSTEM AND METHOD TO ACCELERATE CORE IMAGES ACQUISITION AND PROCESSING USING MACHINE LEARNING

(71) Applicant: ARAMCO SERVICES COMPANY, Houston, TX (US)

(72) Inventors: Tao Lin, Katy, TX (US); Weichang Li, Houston, TX (US); Mokhles M. Mezghani, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 445 days.

(21) Appl. No.: 18/457,145

(22) Filed: Aug. 28, 2023

(65) Prior Publication Data

US 2025/0076272 A1 Mar. 6, 2025

(51) Int. Cl.

| | |
|---|---|
| ***G01N 33/24*** | (2006.01) |
| ***E21B 25/00*** | (2006.01) |
| ***G06T 7/00*** | (2017.01) |

(52) U.S. Cl.

CPC ............. *G01N 33/24* (2013.01); *E21B 25/00* (2013.01); *G06T 7/0002* (2013.01); *G06T 2207/20081* (2013.01); *G06T 2207/30168* (2013.01)

(58) Field of Classification Search

CPC ....... G01N 33/24; E21B 25/00; G06T 7/0002; G06T 2207/20081; G06T 2207/30168

See application file for complete search history.

(56) References Cited

U.S. PATENT DOCUMENTS

| | | | | |
|---|---|---|---|---|
| 10,621,435 | B2 * | 4/2020 | Bridges | G06V 20/20 |
| 2013/0259190 | A1 * | 10/2013 | Walls | G01N 23/046 382/109 |
| 2014/0236486 | A1 * | 8/2014 | Leseur | G01V 9/00 702/11 |
| 2019/0259136 | A1 * | 8/2019 | Shpalensky | G06T 3/4053 |
| 2021/0132026 | A1 * | 5/2021 | Nie | G01N 33/24 |
| 2021/0190664 | A1 * | 6/2021 | Duke | G06T 3/4007 |
| 2022/0098972 | A1 | 3/2022 | Pan et al. | |

FOREIGN PATENT DOCUMENTS

| | | | |
|---|---|---|---|
| EP | 3437067 | B1 | 7/2022 |
| WO | 2022031839 | A1 | 2/2022 |

* cited by examiner

*Primary Examiner* — Alexander Satanovsky

(74) *Attorney, Agent, or Firm* — Osha Bergman Watanabe & Burton LLP

(57) ABSTRACT

A method for analyzing rock cores of a subterranean formation is disclosed. The method includes capturing low resolution core images of the rock cores, selecting, by a computer processor and based on a pre-determined quality threshold for qualifying the low resolution core images, a number of qualified rock cores, capturing high resolution core images of the qualified rock cores, generating, by the computer processor and based on a high resolution core image evaluation model, a ranking of the qualified rock cores, and analyzing, based at least on the ranking, the qualified rock cores to generate a core analysis result.

11 Claims, 8 Drawing Sheets

SYSTEM AND METHOD TO ACCELERATE CORE IMAGES ACQUISITION AND PROCESSING USING MACHINE LEARNING

BACKGROUND

While drilling exploration or development wells, cores are extracted from the subsurface. These cores provide critical information for subsurface characterization. After cores are extracted, they are placed in cylinders and then sent to the laboratory for further analysis and visual examination. For visual examination, the core is slabbed in two parts (for example, ¼ and ¾ for a 4-inches diameter core), and high-resolution images of the slabbed core are acquired at typically around 100 pixels-per-centimeter (PPCM). Those high-resolution photos are examined and analyzed by human geologists and/or computer programs, such as machine learning models, to describe the core with core properties and geological interpretation. However, large oil and gas companies usually drill a large number of wells every year and continue to do so at a similar and even higher rate, which produces millions of feet of core samples to process. It is time and labor consuming of both human operators and automated equipment to acquire, quality control (QC), and process all high-resolution core images to generate core descriptions. In addition, there are huge amount of back logged cores waiting in the work queue, which adds the cost of storage and maintenance, thus delaying the exploration and well development.

SUMMARY

In general, in one aspect, the invention relates to a method for analyzing rock cores of a subterranean formation. The method includes capturing a plurality of low resolution core images of the rock cores, selecting, by a computer processor and based on a pre-determined quality threshold for qualifying the plurality of low resolution core images, a plurality of qualified rock cores, capturing a plurality of high resolution core images of the plurality of qualified rock cores, generating, by the computer processor and based on a high resolution core image evaluation model, a ranking of the plurality of qualified rock cores, and analyzing, based at least on the ranking, the plurality of qualified rock cores to generate a core analysis result.

In general, in one aspect, the invention relates to a core image analyzer for analyzing rock cores of a subterranean formation that includes a processor and a memory coupled to the processor and storing instruction, the instructions, when executed by the processor, comprising functionality for capturing a plurality of low resolution core images of the rock cores, selecting, based on a pre-determined quality threshold for qualifying the plurality of low resolution core images, a plurality of qualified rock cores, capturing a plurality of high resolution core images of the plurality of qualified rock cores, generating, based on a high resolution core image evaluation model, a ranking of the plurality of qualified rock cores, and analyzing, based at least on the ranking, the plurality of qualified rock cores to generate a core analysis result.

In general, in one aspect, the invention relates to a well system that includes a wellbore penetrating a subterranean formation, a well control system of the wellbore, and a core image analyzer comprising functionality for capturing a plurality of low resolution core images of rock cores collected from the wellbore, selecting, based on a pre-determined quality threshold for qualifying the plurality of low resolution core images, a plurality of qualified rock cores, capturing a plurality of high resolution core images of the plurality of qualified rock cores, generating, based on a high resolution core image evaluation model, a ranking of the plurality of qualified rock cores, and analyzing, based at least on the ranking, the plurality of qualified rock cores to generate a core analysis result.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium to accelerate the core image acquisition and processing workflow using machine learning techniques. The accelerated core image workflow enables a faster core analysis to generate core descriptions for subsurface characterization. In one or more embodiments of the invention, a machine learning based approach is used to accomplish the task of fast acquisition and processing of core images. Initially, low-resolution images are captured from the cores with a faster coarse scan. Machine learning models are built to evaluate the coarse images. Based on categories and scores generated from the evaluation, further operation decisions are made based on pre-defined criteria or another machine learning model. The operation decisions may include acquiring high-resolution core images, in which case further machine learning models may be built to evaluate the high-resolution images for processing optimization. The core images are ordered into a process queue based on the categories and scores. Accordingly, the conventional core image analysis is performed according to the process queue.

Figure 1A:
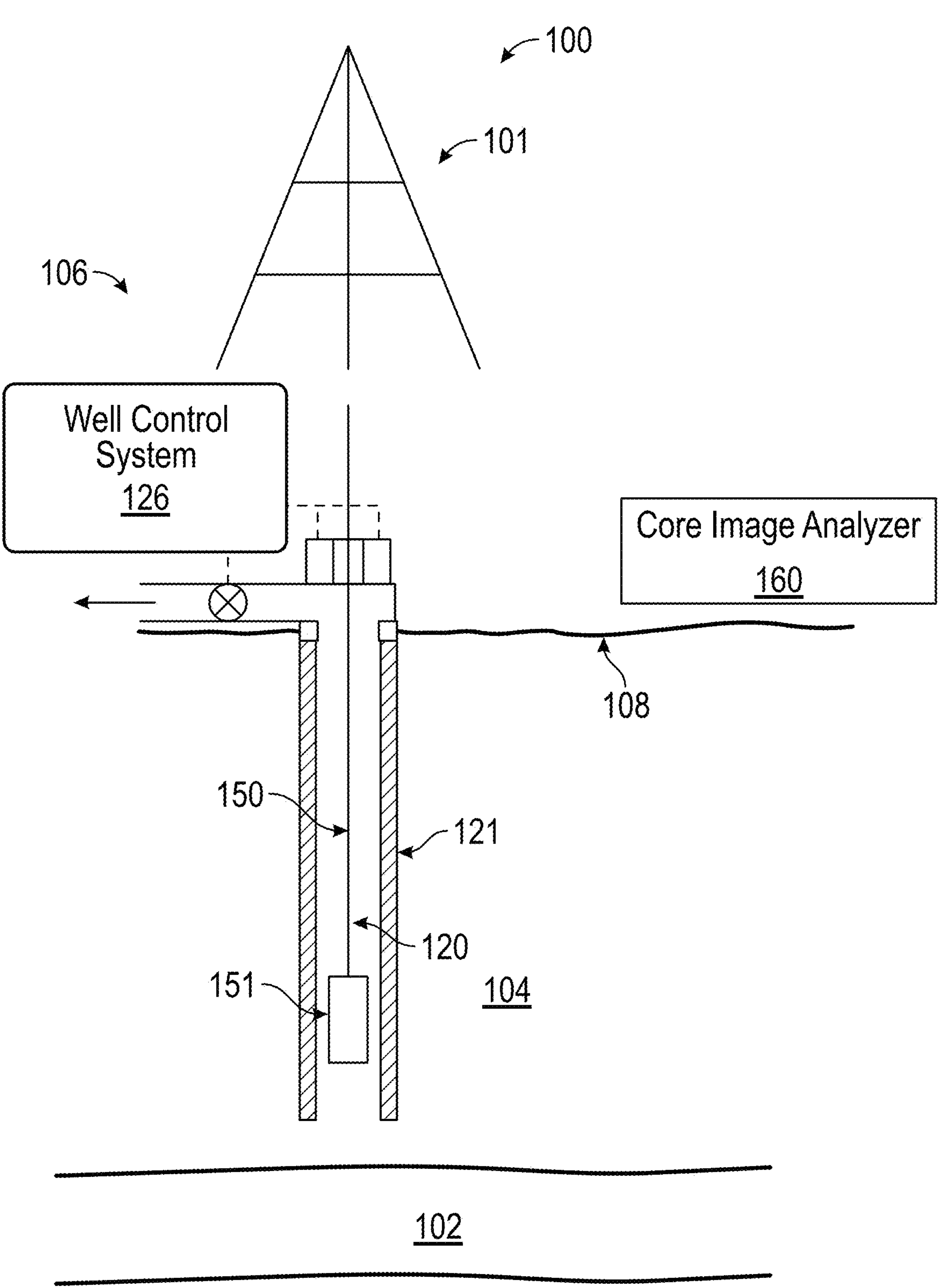
FIGS. 1A-1B show a system in accordance with one or more embodiments.

FIG. 1A shows a schematic diagram in accordance with one or more embodiments. As shown in FIG. 1A, a well environment (100) includes a subterranean formation ("formation") (104) and a well system (106). The area where the well system (106) is located is referred to as the well site. The formation (104) may include a porous or fractured rock formation that resides underground, beneath the earth's surface ("surface") (108). The formation (104) may include different layers of rock having varying characteristics, such as varying degrees of permeability, porosity, capillary pressure, and resistivity. In the case of the well system (106) being a hydrocarbon well, the formation (104) may include a hydrocarbon-bearing reservoir (102). In the case of the well system (106) being operated as a production well, the well system (106) may facilitate the extraction of hydrocarbons (or "production") from the reservoir (102).

In some embodiments disclosed herein, the well system (106) includes a rig (101), a wellbore (120) with a casing (121), a well control system (126), and a core image analyzer (160). The well control system (126) may control various operations of the well system (106), such as well production operations, well drilling operation, well completion operations, well maintenance operations, and reservoir monitoring, assessment and development operations. In one or more embodiments, the well control system (126) performs these functionalities cooperatively with the core image analyzer (160) using the method described in reference to FIGS. 2A-2E below. In some embodiments, the well control system (126) includes a computer system, such as a portion of the computing system described in reference to FIG. 4 below.

The rig (101) is the machine used to drill a borehole to form the wellbore (120). Major components of the rig (101) include the drilling fluid tanks, the drilling fluid pumps (e.g., rig mixing pumps), the derrick or mast, the draw works, the rotary table or top drive, the drill string, the power generation equipment and auxiliary equipment. Drilling fluid, also referred to as "drilling mud" or simply "mud," is used to facilitate drilling boreholes into the earth, such as drilling oil and natural gas wells. The main functions of drilling fluids include providing hydrostatic pressure to prevent formation fluids from entering into the borehole, keeping the drill bit cool and clean during drilling, carrying out drill cuttings, and suspending the drill cuttings while drilling is paused and when the drilling assembly is brought in and out of the borehole.

The wellbore (120) includes a bored hole (i.e., borehole) that extends from the surface (108) towards a target zone of the formation (104), such as the reservoir (102). An upper end of the wellbore (120), terminating at or near the surface (108), may be referred to as the "up-hole" end of the wellbore (120), and a lower end of the wellbore, terminating in the formation (104), may be referred to as the "downhole" end of the wellbore (120). The wellbore (120) may facilitate the circulation of drilling fluids during drilling operations for the wellbore (120) to extend towards the target zone of the formation (104) (e.g., the reservoir (102)), facilitate the flow of hydrocarbon production (e.g., oil and gas) from the reservoir (102) to the surface (108) during production operations, facilitate the injection of substances (e.g., water) into the hydrocarbon-bearing formation (104) or the reservoir (102) during injection operations, or facilitate the communication of monitoring devices (e.g., logging tools) lowered into the formation (104) or the reservoir (102) during monitoring operations (e.g., during in situ logging operations).

In some embodiments, the well system (106) is provided with a bottom hole assembly (BHA) (151) attached to the drill string (150) to suspend into the wellbore (120) for performing the well drilling operation. The bottom hole assembly (BHA) is the lowest part of a drill string and includes the drill bit, drill collar, stabilizer, mud motor, etc. During the drilling operation, core samples or rock cores may be extracted using a downhole coring bit and brought to the surface (108) for analysis.

In some embodiments, the core image analyzer (160) may include hardware and/or software with functionality for generating core descriptions of rock cores. For example, the core image analyzer (160) may store core images regarding core samples for performing analysis. The core image analyzer (160) may further analyze the core images to generate and/or update corresponding core descriptions. While the core image analyzer (160) is shown at a well site, at least a portion of the core image analyzer (160) may be located away from well sites. In some embodiments, the core image analyzer (160) may include a computer system that is similar to the computer system (400) described below with regard to FIG. 4 and the accompanying description.

Figure 1B:
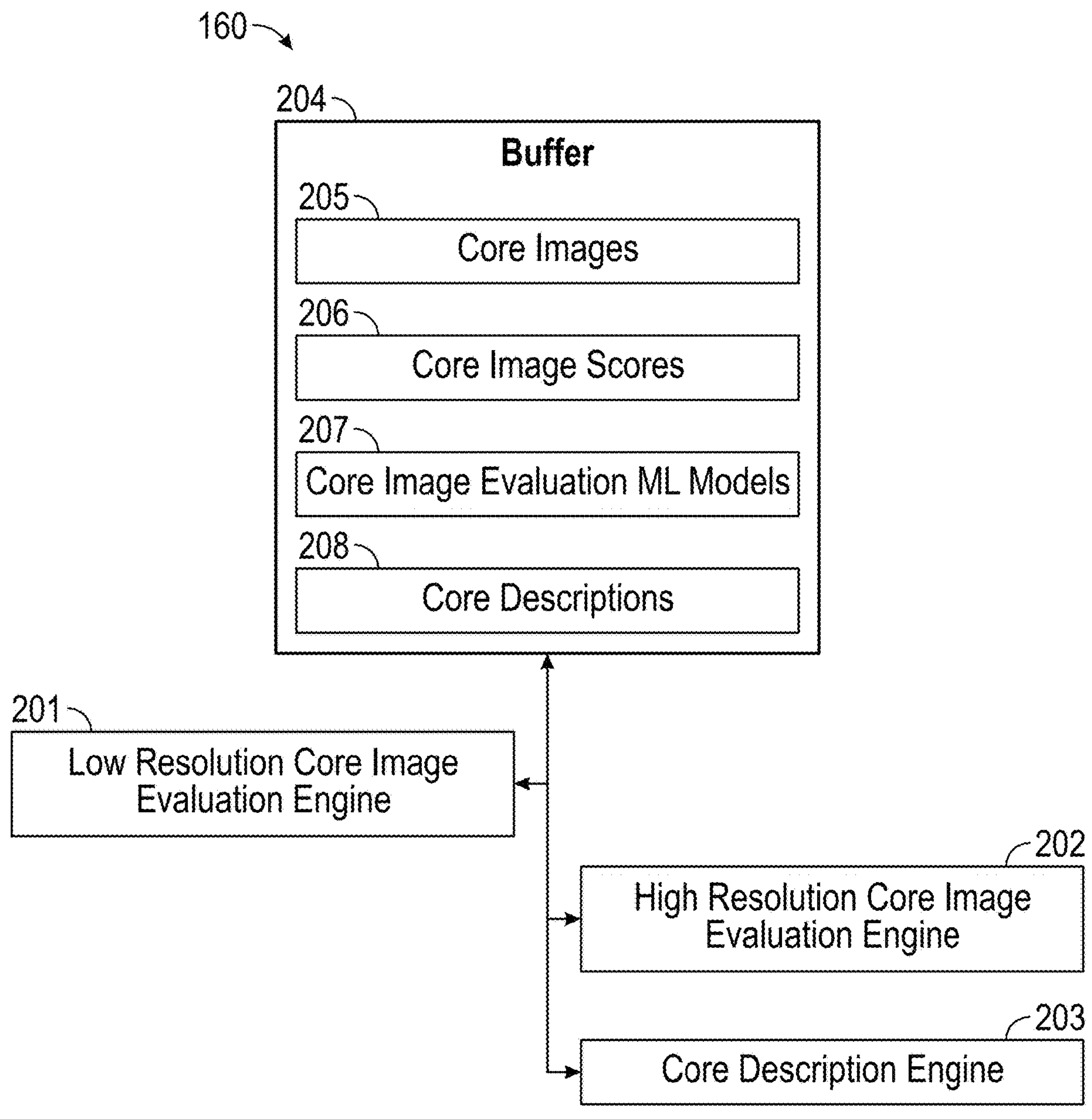

Turning to FIG. 1B, FIG. 1B shows a schematic diagram in accordance with one or more embodiments. In one or more embodiments, one or more of the modules and/or elements shown in FIG. 1B may be omitted, repeated, and/or substituted. Accordingly, embodiments of the invention should not be considered limited to the specific arrangements of modules and/or elements shown in FIG. 1B.

As shown in FIG. 1B, FIG. 1B illustrates the core image analyzer (160) that has multiple components, including, for example, a buffer (204), a low resolution core image evaluation engine (201), a high resolution core image evaluation engine (202), and a core description engine (203). Each of these components (201, 202, 203, 204) may be located on the same computing device (e.g., personal computer (PC), laptop, tablet PC, smart phone, multifunction printer, kiosk, server, etc.) or on different computing devices that are connected via a network, such as a wide area network or a portion of Internet of any size having wired and/or wireless segments. Each of these components is discussed below.

In one or more embodiments of the invention, the buffer (204) may be implemented in hardware (i.e., circuitry), software, or any combination thereof. The buffer (204) is configured to store data generated and/or used by the core image analyzer (160). The data stored in the buffer (204) includes the core images (205), the core image scores (206), the core image evaluation models (207), and the core descriptions (208).

The core images (205) are photographs of rock cores. The core images (205) include photographs of a number of rock core columns, referred to as core plugs, collected from different geographical locations throughout an area of interest. Each rock core column is a sequence of rock cores extending across a depth range of interest in the borehole. In particular, each rock core is marked to indicate the locations and depths such that the markings are captured in the corresponding core image. In one or more embodiments of the invention, the core images (205) are captured using a high speed configuration of automated core imaging equipment, an onsite camera the well site, or aerial imaging by drones. The core images (205) include low resolution core images or coarse core images where the resolution is selected to resolve core quality, such as missing segment, covered segment, illumination, contrast, etc. For example, the coarse core images may be captured with the resolution of 16 PPCM in some acquisition configuration. However, this may vary with different acquisition instruments. The core images (205) further include high resolution core images where the resolution is selected to reveal important features (e.g., porosity, grain density) for core analysis. For example, high resolution images may be captured with the resolution of 100 pixels-per-centimeter (PPCM).

The core image scores (206) include quality scores and importance scores assigned to the core images (205). Specifically, each low quality core image is assigned a quality score indicating whether the corresponding rock core is worthy of the time and effort in capturing high resolution core image for core analysis. Each high quality core image is assigned an importance score indicating a level of importance of the high resolution core image for core analysis.

The core image evaluation machine learning (ML) models (207) are machine learning models and include a low resolution core image evaluation model and a high resolution core image evaluation model. The applicable ML models depend on the available data. For example, the classification algorithms can be used for categorical labels, and regression algorithms can be used for numerical labels. Example of classification algorithms includes Random Forest classifier. Example of regression algorithms includes Convolutional Neural Network. Specifically, the low resolution core image evaluation model is configured to recognize quality levels of the low resolution core images and generate corresponding quality scores. The high resolution core image evaluation model is configured to recognize importance levels of the high resolution core image as related to core analysis and generate corresponding importance scores.

In one or more embodiments of the invention, each of the low resolution core image evaluation engine (201), high resolution core image evaluation engine (202), and core description engine (203) may be implemented in hardware (i.e., circuitry), software, or any combination thereof. The low resolution core image evaluation engine (201) is configured to construct a coarse core image training dataset and generate quality scores for new (i.e., unprocessed) coarse core images. The high resolution core image evaluation engine (202) is configured to construct a high resolution core image training dataset and generate importance scores for new (i.e., unprocessed) high quality core images.

In one or more embodiments of the invention, the core description engine (203) is configured to analyze the high resolution core images and generate corresponding core descriptions according to a priority scheme based on the importance scores.

In one or more embodiments, the core image analyzer (160) performs the functionalities described above using the method described in reference to FIGS. 2A-2E below. Although the core image analyzer (160) is shown as having three engines (201, 202, 203), in other embodiments of the invention, the core image analyzer (160) may have more or fewer engines and/or more or fewer other components. Further, the functionality of each component described above may be split across components. Further still, each component (201, 202, 203) may be utilized multiple times to carry out an iterative operation.

FIGS. 2A-2E show flowcharts in accordance with one or more embodiments. Specifically, FIGS. 2A-2E describe a method of generating core descriptions by accelerating core image analysis based on a machine learning based approach for fast acquisition and processing of core images. A field operation is then performed according to the generated core descriptions. One or more blocks in FIGS. 2A-2E may be performed using one or more components as described in FIGS. 1A-1B. While the various blocks in FIGS. 2A-2E are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Figure 2A:
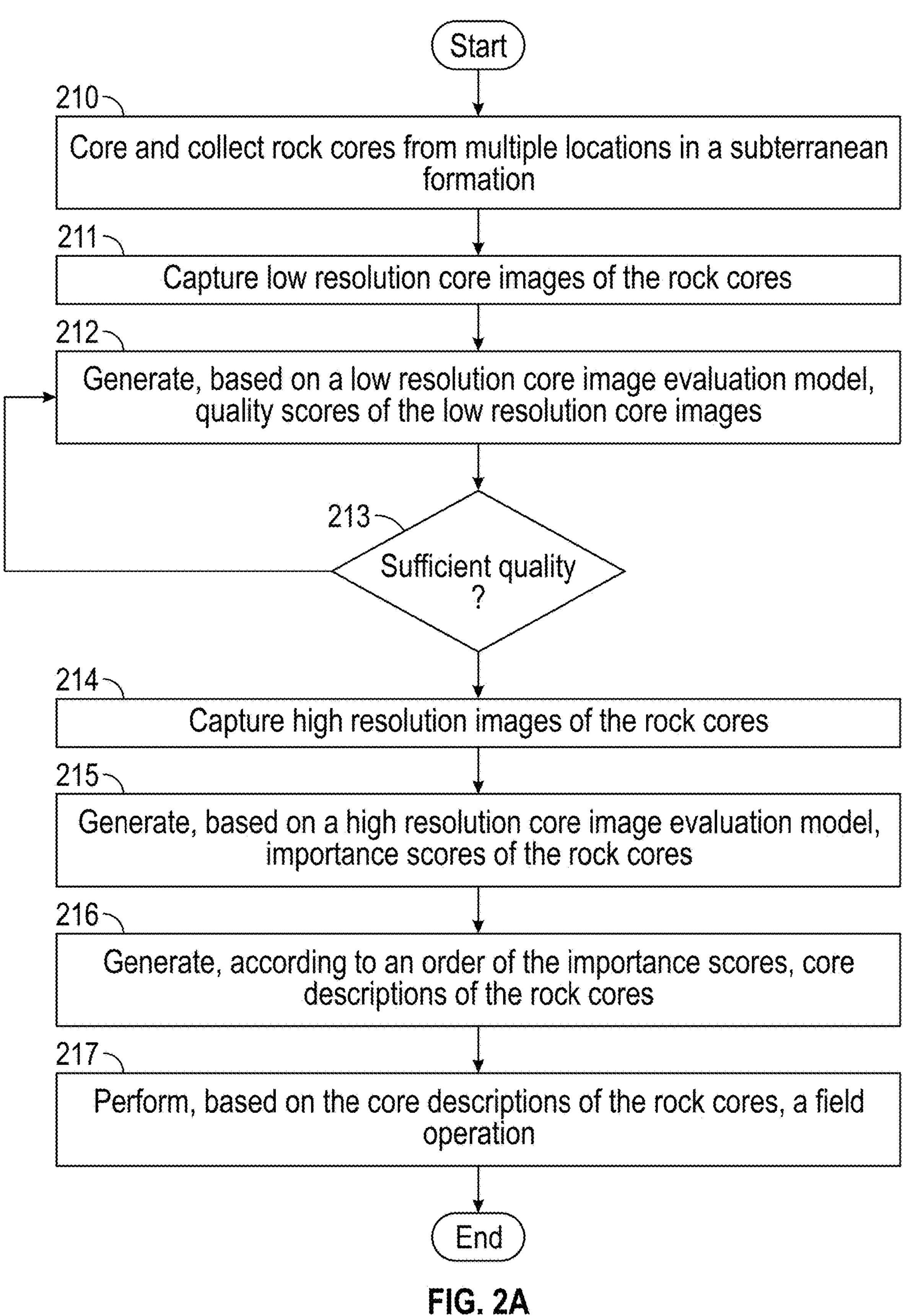
FIGS. 2A-2E show flow diagrams in accordance with one or more embodiments.
Figure 3A:
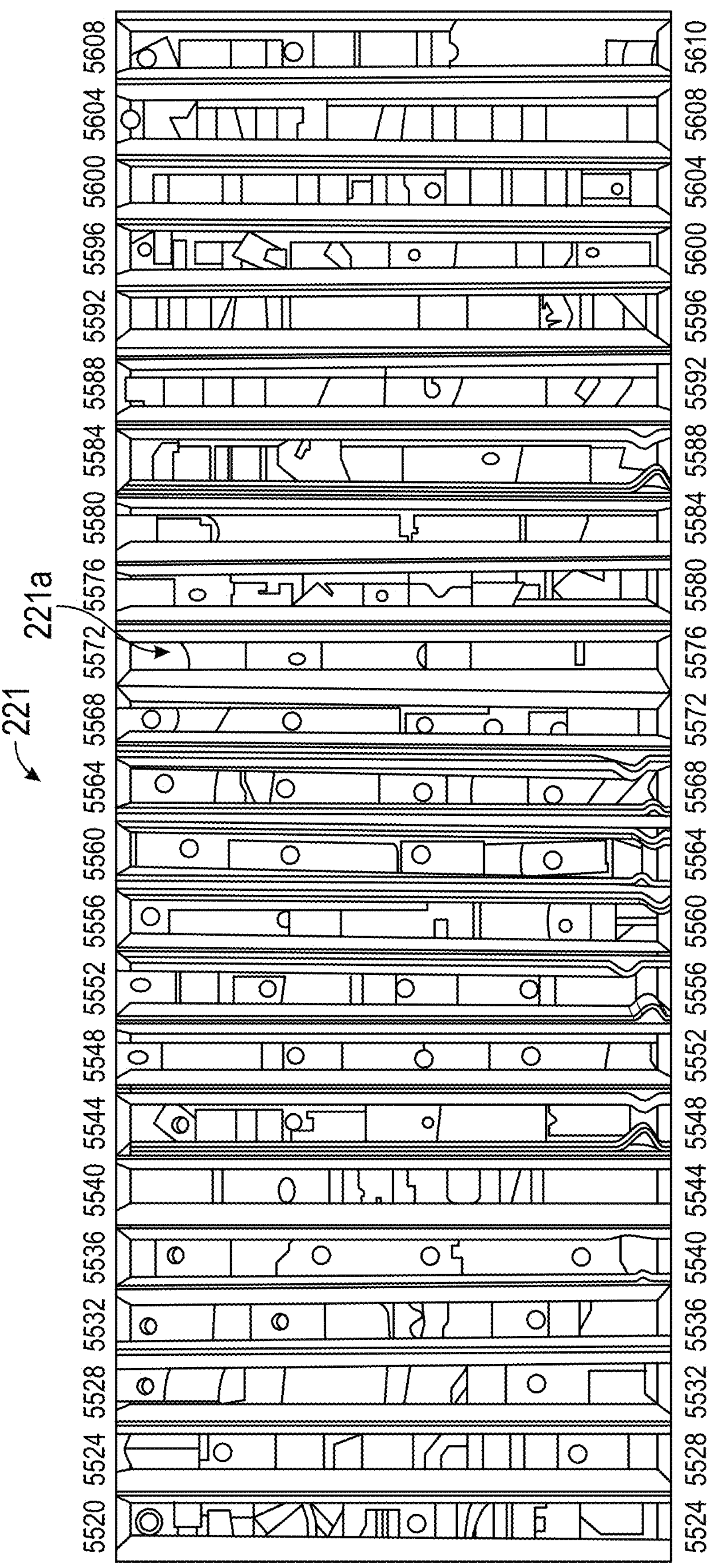
FIGS. 3A-3B show an example in accordance with one or more embodiments.

Turning to FIG. 2A, initially in Block 210, coring is performed to extract rock cores from a number of geographical locations in an area of interest of the subterranean formation. The extracted rock cores are slabbed to prepare core plugs with specific dimensions, typically about 25.4-38.1 mm in diameter and a length 1-1.5 times greater than the diameter. The slabbed and plugged rock cores are then marked and organized according to respective depths and locations where the rock cores are collected. An example of slabbed and plugged cores is shown in FIG. 3A.

Figure 2B:
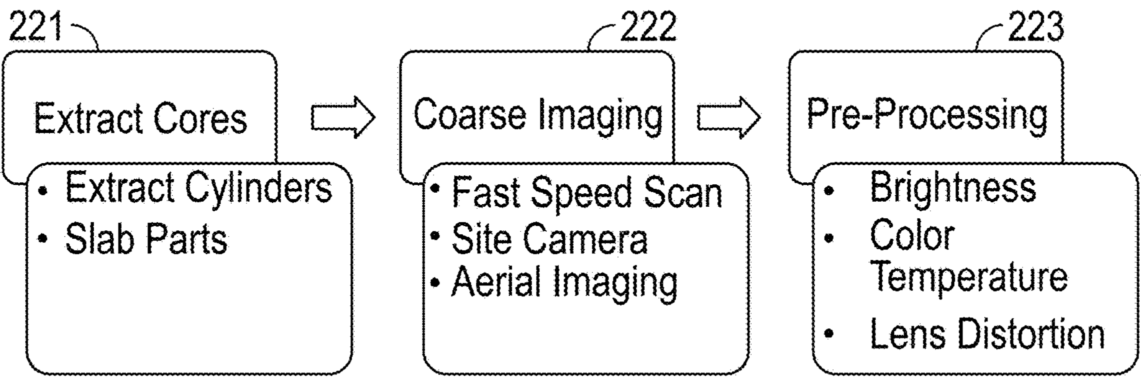

In Block 211, low resolution photographs (i.e., coarse core images) of the rock cores are captured by a fast imaging approach using, e.g., a high speed configuration of automated core imaging equipment, an onsite camera the wellsite, and/or aerial imaging by drones. Image pre-processing may be performed to normalize the images, such as illumination/brightness compensation, color temperature calibration, lens distortion correction, etc. Markings on the rock cores are captured in each low resolution core image to facilitate subsequent retrieval of corresponding rock cores. An example workflow to capture the coarse core images is shown in FIG. 2B below.

Figure 2C:
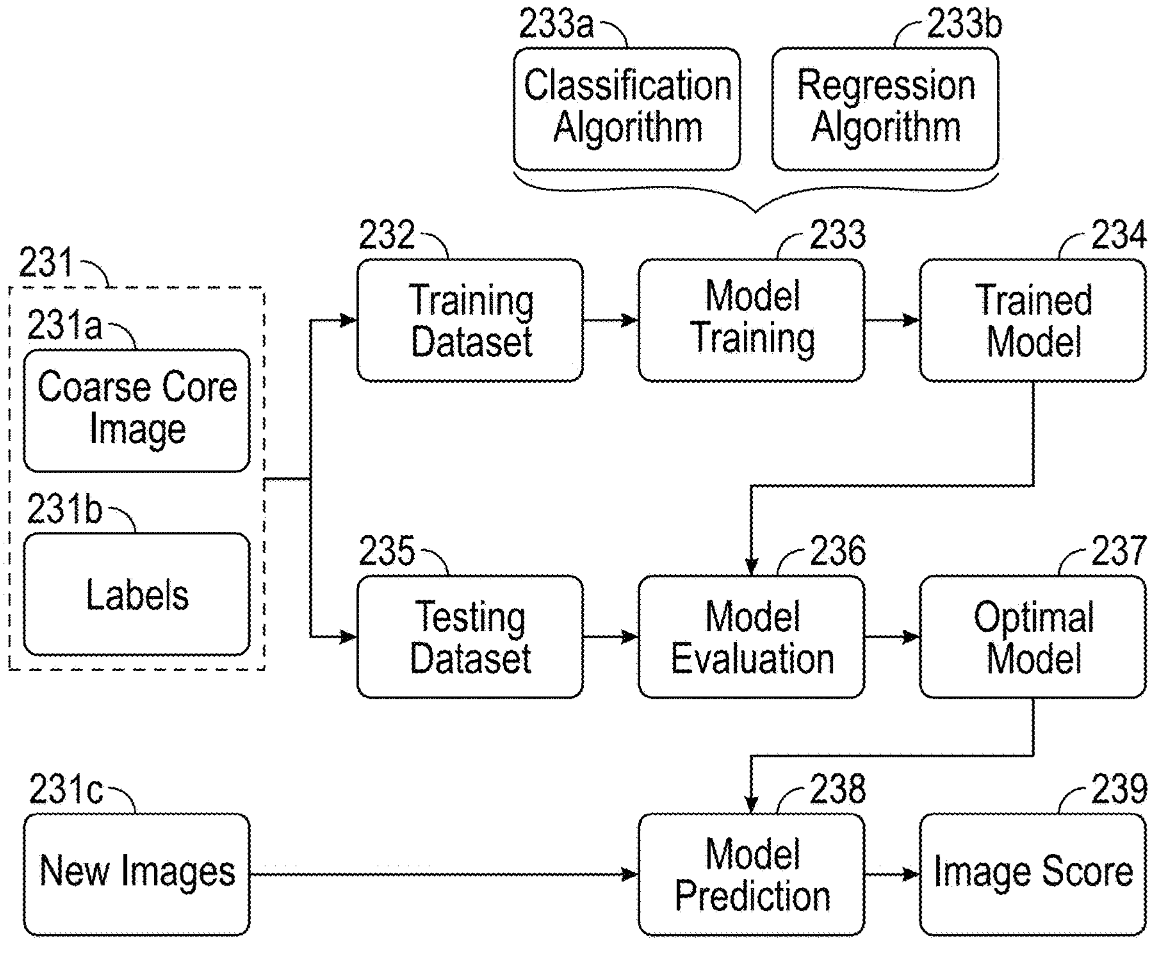

In Block 212, quality scores of the low resolution core images are generated based on a low resolution core image evaluation model. In one or more embodiments, the low resolution core image evaluation model is a machine learning model constructed to evaluate the coarse core images. An example workflow to construct the machine learning model for coarse core image evaluation is shown in FIG. 2C below.

Figure 2D:
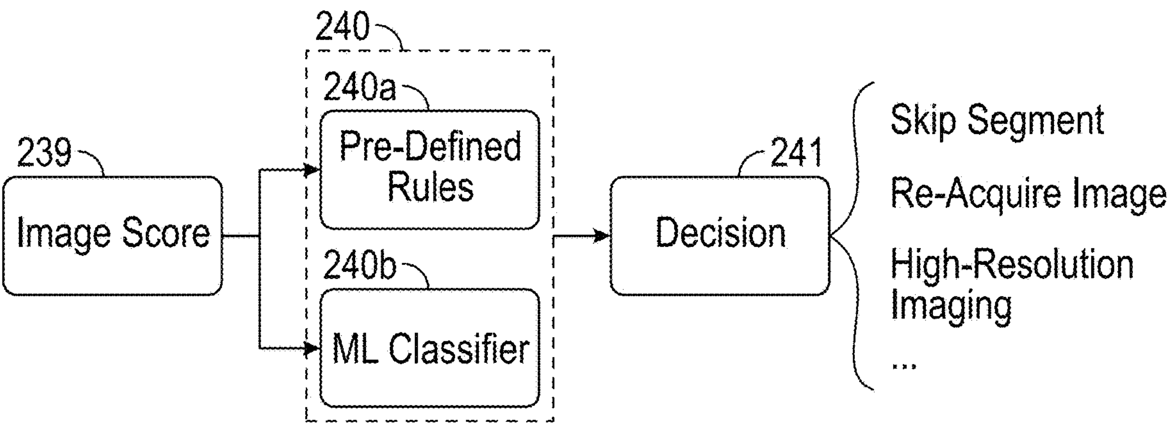

In Block 213, a determination is made as to whether a particular low resolution core image has sufficient quality, i.e., having a quality score that exceeds a pre-determined threshold. If the determination is positive, i.e., the quality score of the particular low resolution core images exceeds the pre-determined threshold, the method proceeds to Block 214. If the determination is negative, i.e., the quality score of the particular low resolution core images is below the pre-determined threshold, the method returns to Block 212 to process another low resolution core image. An example model of making the determination is shown in FIG. 2D below.

Figure 3B:
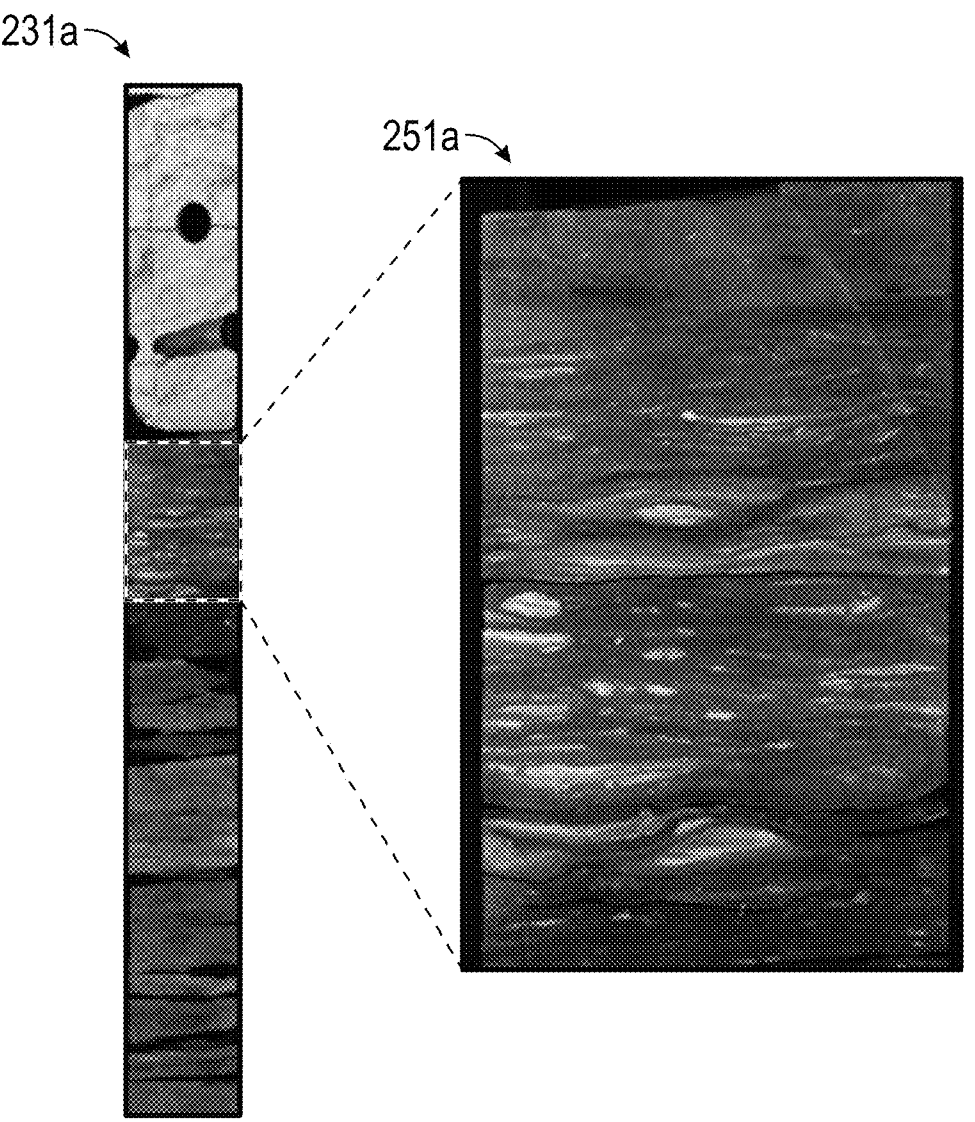

In Block 214, high resolution photographs (i.e., high resolution core images) of the rock cores with sufficient qualities are captured. Such high quality rock cores are identified and retrieved based on the markings captured in each low resolution core image having quality score exceeding the pre-determined threshold. The resolution of the high resolution photograph is selected such as to clearly delineate details of the rock core. An example of a high resolution core image is shown in FIG. 3B below.

Figure 2E:
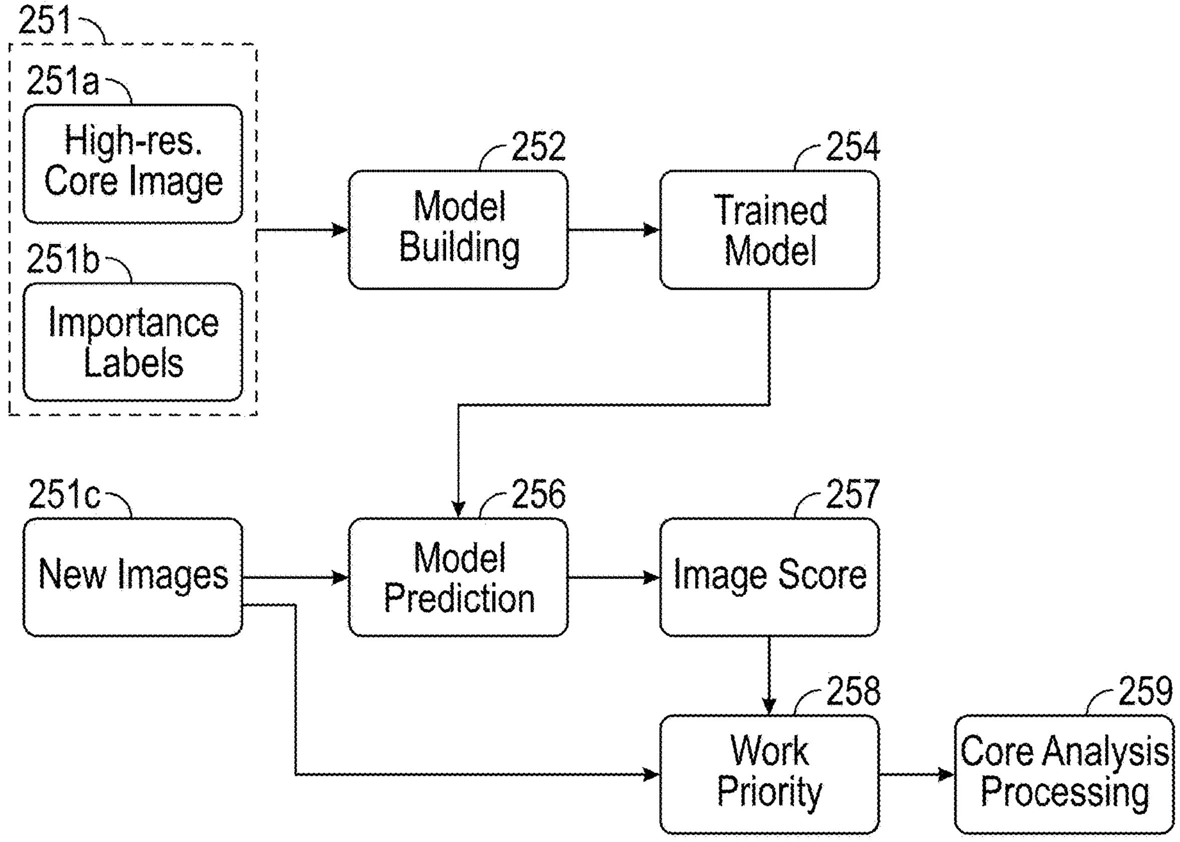

In Block 215, important scores of the high resolution core images are generated based on a high resolution core image evaluation model. In one or more embodiments, the high resolution core image evaluation model is a machine learning model constructed to evaluate the high resolution core images. In one or more embodiments, the importance score is used to prioritize the working queue of high resolution core image analysis and to optimize the core image processing with most critical images. An example workflow to construct and use the machine learning model for high resolution core image evaluation is shown in FIG. 2E below.

In Block 216, core descriptions of the rock cores are generated based on the high resolution core images. In one or more embodiments, the high resolution core images are analyzed according to a priority scheme, such as a work queue based on corresponding importance scores. For example, the core description may indicate the porosity, permeability, fluid saturation, grain density, and other geological characteristics of a corresponding geographical location in the subterranean formation.

In Block 217, a field operation of the subterranean formation is performed based at least on the core descriptions. For example, the field operation may include continuing drilling and/or completing the wellbore, planning and/or initiating production of the wellbore, etc. In another example, exploration and/or development of the wellbore may be discontinued based on the core description. Further, a target location may be selected, based on the core description or other core analysis result, from multiple geographical locations in the area of interest of the subterranean formation. For example, the target location may be selected based on porosity, permeability, fluid saturation, grain density, or other geological characteristics indicated by the core analysis result regarding the target location. Accordingly, the field operation is then performed at the selected target location.

Turning to FIG. 2B, FIG. 2B illustrates an example workflow to capture the coarse core images. Initially in Block 221, cylindrical rock cores are extracted in a downhole location of a wellbore during drilling. The extracted cork cores are slabbed into rock plugs. In Block 222, coarse core images are captured using a high speed image scanner, onsite camera, or ariel imaging device. In Block 223, the coarse core images are pre-processed to adjust brightness, color temperature, and/or lens distortion.

Turning to FIG. 2C, FIG. 2C illustrates an example workflow to construct the machine learning model for coarse core image evaluation. Initially in Block 231, rock core labels (231*b*) are physically marked on at least some of the rock cores and captured within the coarse core images (231*a*). The coarse core images (231*a*) are allocated into a training dataset (232) and a testing dataset (235). Within the training dataset (232), a label of image quality is assigned to and marked on each coarse core image by human experts and/or an existing tool as the ground truth of the machine learning model. The label may be a single score, or groups of scores with subject matter expert (SME) insights, such as core quality, missing segment, covered segment, illumination, contrast, etc. determined by the human experts. The score may be categorical values, such as good/acceptable/bad, or numerical values such as 1~10. The training dataset (232) is used to train a machine learning model (i.e., trained model (234)) during model training (233) based on machine learning algorithms such as the classification algorithm (233*a*) and regression algorithm (233*b*). For example, the classification algorithm (233*a*) may be used for categorical labels, and regression algorithm (233*b*) may be used for numerical labels. Specifically, the trained model (234) is trained and validated during a machine training phase using the training dataset (232) by the chosen algorithms to learn the correlation between the core images and the ground truth labels. The training is performed by minimizing the loss function for the model output and ground truth labels, using metrics such as mean square error (MSE). Optionally, hyper-parameter tuning may be performed to optimize the model performance.

After the model training and validation, the trained model (234) is applied to the testing dataset (235) to evaluate the model performance, i.e., model evaluation (236). Either same or different metrics as the training may be used in the evaluation. The trained model (234) is deployed as the optimal model (237) when the model performance is validated. The optimal model (237) is then applied to the new (i.e., unprocessed) coarse core images (231*c*) to generate model prediction (238) (i.e., predict the quality scores) of the new coarse images (231*c*).

Turning to FIG. 2D, FIG. 2D illustrates an example decision model (240) for making the determination regarding coarse core images. As shown in FIG. 2D, the decision model (240) is built from the coarse core image quality scores (239), described in reference to FIG. 2C above, to decide further action on the core description workflow. The model (240) may be built by pre-defined rules (240*a*) from expert knowledge, or by a machine learning based classifier (240*b*) to predict the decision outcomes. For example, if the coarse core image quality score is identified as bad and is not worthy of any further analysis, the decision (241) may be (i) to skip this segment of rock cores without acquiring high-resolution core images, or (ii) to re-acquire the coarse core images for re-evaluation. Based on the decision model (240), only the rock cores with satisfactory coarse core image quality scores are chosen to take high resolution core images. The overall core description workflow is accelerated by eliminating unnecessary high-resolution image acquisition as they are time and labor consuming.

Turning to FIG. 2E, FIG. 2E illustrates an example workflow to construct and use the machine learning model for high resolution core image evaluation. Initially, a high resolution core image training dataset (251) is constructed where importance labels (251*b*) are assigned to high resolution core images (251*a*) by human experts and/or an existing tool as the ground truth of the high resolution core image evaluation machine learning model. The label may be a single score, or groups of scores with subject matter expert (SME) insights, such as core quality (good/acceptable/bad, or numerical), missing segment, covered segment, illumination, contrast, etc., that are determined as a measure of importance by the human experts. The ground truth score may be categorical values, such as high/medium/low, or numerical values such as 1~10 that is used to train a machine learning model (i.e., trained model (254)). Similar to the low resolution core image evaluation model described in reference to FIG. 2C above, the model building (252) of the high resolution core image evaluation model is performed during a machine training phase and may be based on machine learning algorithms such as classification algorithms and regression algorithms. For example, classification algorithms may be used for categorical labels, and regression algorithms may be used for numerical labels. Specifically, the trained model (234) is trained and validated with the training dataset (251) by the chosen algorithms to learn the correlation between the high resolution core images and the ground truth labels. The training is performed by minimizing the loss function for the model output and ground truth labels, using metrics such as mean square error (MSE). Optionally, hyper-parameter tuning may be performed to optimize the model performance.

After the model training and validation, the trained model (254) is applied during model prediction (256) to the new (i.e., unprocessed) high resolution core images (251*c*) to generate and assign the importance scores (257) to the new high resolution core images (251*c*). Accordingly, the new high resolution core images (251*c*) may be organized into a work priority queue (258) of core analysis processing (259) according to the importance scores (257). In other words, a ranking may be generated to order the new high resolution core images (251*c*) from the highest importance score to the lowest importance score. Accordingly, the work priority queue (258) organizes the new high resolution core images (251*c*) according to the ranking where the core image with higher importance score is processed with higher priority ahead of another core image with lower importance score. Core descriptions of the new high resolution core images (251*c*) are generated during the core analysis processing (259).

Turning to FIG. 3A, FIG. 3A illustrates an example of the extracted cores (221) described in reference to FIG. 2B above. As shown in FIG. 3A, individual core plugs (e.g., core plug (221*a*)) are marked and organized in the collection of extracted cores (221) according to the respective extracted depths and locations.

Turning to FIG. 3B, FIG. 3B illustrates an example of the coarse core image (231*a*) and high resolution core image (251*a*) described in reference to FIGS. 2C and 2E above. As shown in FIG. 3B, the high-resolution core image (251*a*) is acquired at a typical resolution around 100 pixels-per-centimeter (PPCM).

Figure 4:
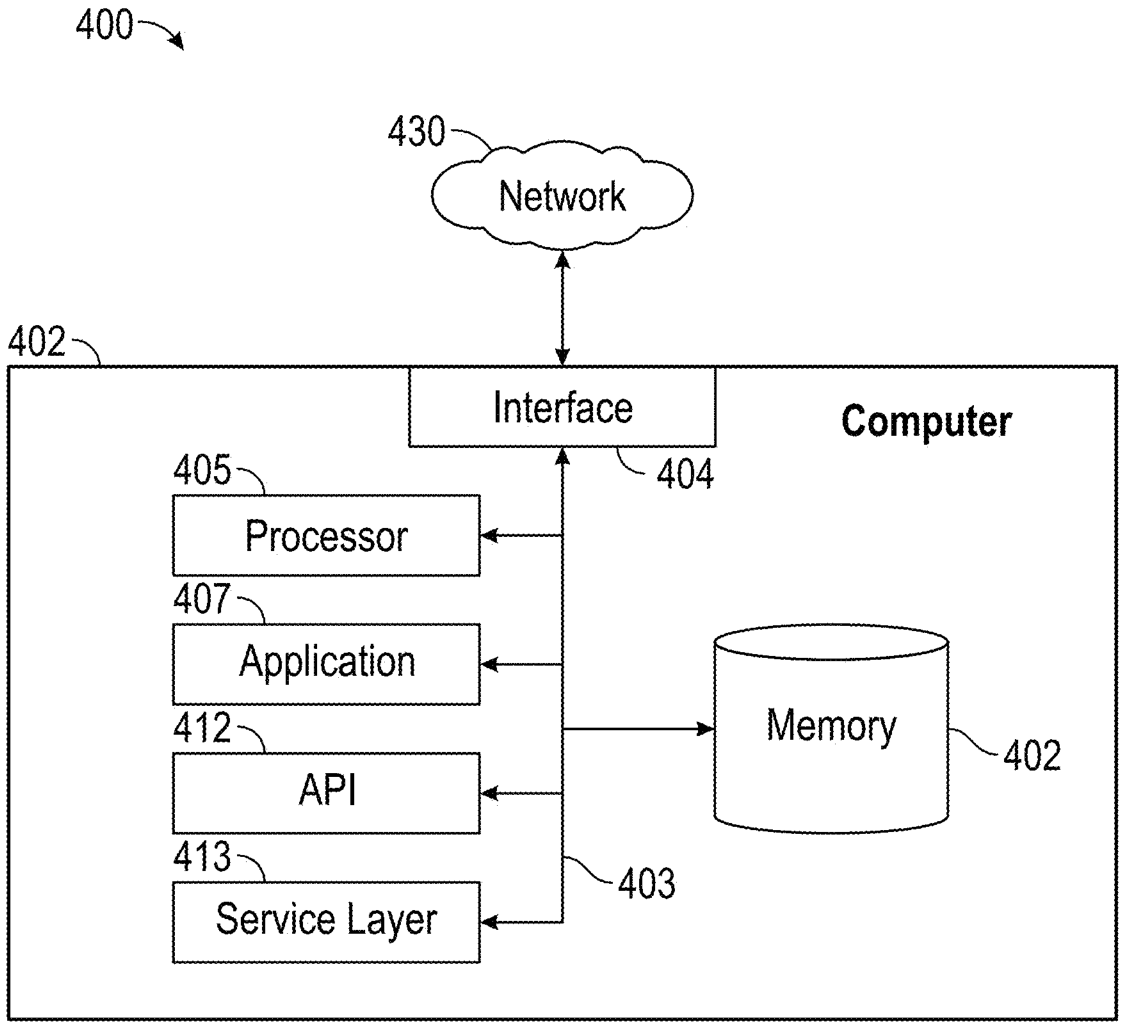
FIG. 4 shows a computing system in accordance with one or more embodiments.

Embodiments may be implemented on a computer system. FIG. 4 is a block diagram of a computer system (400) used to provide computational functionalities associated with described algorithms, methods, functions, processes, flows, and procedures as described in the instant disclosure, according to an implementation. The illustrated computer (402) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (402) may include a computer that includes an input device, such as a keypad, keyboard, touch screen, or other device that can accept user information, and an output device that conveys information associated with the operation of the computer (402), including digital data, visual, or audio information (or a combination of information), or a GUI.

The computer (402) can serve in a role as a client, network component, a server, a database or other persistency, or any other component (or a combination of roles) of a computer system for performing the subject matter described in the instant disclosure. The illustrated computer (402) is communicably coupled with a network (430). In some implementations, one or more components of the computer (402) may be configured to operate within environments, including cloud-computing-based, local, global, or other environment (or a combination of environments).

At a high level, the computer (402) is an electronic computing device operable to receive, transmit, process, store, or manage data and information associated with the described subject matter. According to some implementations, the computer (402) may also include or be communicably coupled with an application server, e-mail server, web server, caching server, streaming data server, business intelligence (BI) server, or other server (or a combination of servers).

The computer (402) can receive requests over network (430) from a client application (for example, executing on another computer (402)) and responding to the received requests by processing the said requests in an appropriate software application. In addition, requests may also be sent to the computer (402) from internal users (for example, from a command console or by other appropriate access method), external or third-parties, other automated applications, as well as any other appropriate entities, individuals, systems, or computers.

Each of the components of the computer (402) can communicate using a system bus (403). In some implementations, any or all of the components of the computer (402), both hardware or software (or a combination of hardware and software), may interface with each other or the interface (404) (or a combination of both) over the system bus (403) using an application programming interface (API) (412) or a service layer (413) (or a combination of the API (412) and service layer (413). The API (412) may include specifications for routines, data structures, and object classes. The API (412) may be either computer-language independent or dependent and refer to a complete interface, a single function, or even a set of APIs. The service layer (413) provides software services to the computer (402) or other components (whether or not illustrated) that are communicably coupled to the computer (402). The functionality of the computer (402) may be accessible for all service consumers using this service layer. Software services, such as those provided by the service layer (413), provide reusable, defined business functionalities through a defined interface. For example, the interface may be software written in JAVA, C++, or other suitable language providing data in extensible markup language (XML) format or other suitable format. While illustrated as an integrated component of the computer (402), alternative implementations may illustrate the API (412) or the service layer (413) as stand-alone components in relation to other components of the computer (402) or other components (whether or not illustrated) that are communicably coupled to the computer (402). Moreover, any or all parts of the API (412) or the service layer (413) may be implemented as a child or sub-modules of another software module, enterprise application, or hardware module without departing from the scope of this disclosure.

The computer (402) includes an interface (404). Although illustrated as a single interface (404) in FIG. 4, two or more interfaces (404) may be used according to particular needs, desires, or particular implementations of the computer (402). The interface (404) is used by the computer (402) for communicating with other systems in a distributed environment that are connected to the network (430). Generally, the interface (404) includes logic encoded in software or hardware (or a combination of software and hardware) and operable to communicate with the network (430). More specifically, the interface (404) may include software supporting one or more communication protocols associated with communications such that the network (430) or interface's hardware is operable to communicate physical signals within and outside of the illustrated computer (402).

The computer (402) includes at least one computer processor (405). Although illustrated as a single computer processor (405) in FIG. 4, two or more processors may be used according to particular needs, desires, or particular implementations of the computer (402). Generally, the computer processor (405) executes instructions and manipulates data to perform the operations of the computer (402) and any algorithms, methods, functions, processes, flows, and procedures as described in the instant disclosure.

The computer (402) also includes a memory (406) that holds data for the computer (402) or other components (or a combination of both) that can be connected to the network (430). For example, memory (406) can be a database storing data consistent with this disclosure. Although illustrated as a single memory (406) in FIG. 4, two or more memories may be used according to particular needs, desires, or particular implementations of the computer (402) and the described functionality. While memory (406) is illustrated as an integral component of the computer (402), in alternative implementations, memory (406) can be external to the computer (402).

The application (407) is an algorithmic software engine providing functionality according to particular needs, desires, or particular implementations of the computer (402), particularly with respect to functionality described in this disclosure. For example, application (407) can serve as one or more components, modules, applications, etc. Further, although illustrated as a single application (407), the application (407) may be implemented as multiple applications (407) on the computer (402). In addition, although illustrated as integral to the computer (402), in alternative implementations, the application (407) can be external to the computer (402).

There may be any number of computers (402) associated with, or external to, a computer system containing computer (402), each computer (402) communicating over network (430). Further, the term "client," "user," and other appropriate terminology may be used interchangeably as appropriate without departing from the scope of this disclosure. Moreover, this disclosure contemplates that many users may use one computer (402), or that one user may use multiple computers (402).

In some embodiments, the computer (402) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AlaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method comprising:

capturing a training dataset comprising a plurality of coarse core images of a plurality of rock cores and a plurality of rock core labels associated with the plurality of coarse core images;

performing a training operation on a convolutional neural network using the training dataset and a regression algorithm to produce a trained model, wherein the trained model determines one or more predicted image scores in response to receiving one or more core images, and wherein the one or more predicted image scores are used to determine a selection among a plurality of image processing operations;

determining, by a computer processor, a predicted image score using the trained model and a coarse core image of a rock core;

determining, by the computer processor, a selected image processing operation among the plurality of image processing operations based on the predicted image score, wherein the selected image processing operation corresponds to an image acquisition of the rock core at a higher resolution than the coarse core image; and capturing, by a camera and in response to determining the selected image processing operation, a higher resolution core image of the rock core; and determining, by the computer processor, a permeability or a porosity of the rock core using the higher resolution core image.

2. The method according to claim 1, further comprising:

performing, based on the permeability or the porosity of the rock core, a field operation of a subterranean formation.

3. The method according to claim 2, further comprising:

coring and collecting the plurality of rock cores from a plurality of geographical locations in the subterranean formation; and selecting, from the plurality of geographical locations and based on the permeability or the porosity of the rock core, a target location, wherein the field operation is performed at the target location.

4. The method according to claim 1, wherein the higher resolution core image is used to determine one or more of porosity, permeability, fluid saturation and grain density.

5. A core image analyzer, comprising:

a processor; and a memory coupled to the processor and storing instructions, the instructions, when executed by the processor, being configured to perform a method comprising:

capturing a training dataset comprising a plurality of coarse core images of a plurality of rock cores and a plurality of rock core labels associated with the plurality of coarse core images;

performing a training operation on a convolutional neural network using the training dataset and a regression algorithm to produce a trained model, wherein the trained model determines one or more predicted image scores in response to receiving one or more core images, and wherein the one or more predicted image scores are used to determine a selection among a plurality of image processing operations;

determining a predicted image score using the trained model and a coarse core image of a rock core;

determining a selected image processing operation among the plurality of image processing operations based on the predicted image score, wherein the selected image processing operation corresponds to an image acquisition of the rock core at a higher resolution than the coarse core image; and capturing, by a camera and in response to determining the selected image processing operation, a higher resolution core image of the rock core; and determining a permeability or a porosity of the rock core using the higher resolution core image.

6. The core image analyzer according to claim 5, wherein the method further comprises:

performing, based on the permeability or the porosity of the rock core, a field operation of a subterranean formation.

7. The core image analyzer according to claim 6, wherein the method further comprises:

selecting, from a plurality of geographical locations and based on the permeability or the porosity of the rock core, a target location, wherein the plurality of rock cores are cored and collected from the plurality of geographical locations in the subterranean formation, wherein the field operation is performed at the target location.

8. The core image analyzer according to claim 5, wherein the higher resolution core image is used to determine one or more of fluid saturation and grain density.

9. A well system, comprising:

a wellbore penetrating a subterranean formation at a well site;

a well control system of the wellbore; and a core image analyzer comprising a processor and a memory, wherein the core image analyzer is configured to perform a method comprising:

capturing a training dataset comprising a plurality of coarse core images of a plurality of rock cores and a plurality of rock core labels associated with the plurality of coarse core images;

performing a training operation on a convolutional neural network using the training dataset and a regression algorithm to produce a trained model, wherein the trained model determines one or more predicted image scores in response to receiving one or more core images, and wherein the one or more predicted image scores are used to determine a selection among a plurality of image processing operations;

determining a predicted image score using the trained model and a coarse core image of a rock core;

determining a selected image processing operation among the plurality of image processing operations based on the predicted image score, wherein the selected image processing operation corresponds to an image acquisition of the rock core at a higher resolution than the coarse core image; and capturing, by a camera and in response to determining the selected image processing operation, a higher resolution core image of the rock core; and determining a permeability or a porosity of the rock core using the higher resolution core image.

10. The well system according to claim 9, the well control system comprising functionality for:

performing, based on the permeability or the porosity of the rock core, a field operation of a subterranean formation.

11. The well system according to claim 10, wherein the method further comprises:

selecting, from a plurality of geographical locations and based on the permeability or the porosity of the rock core, the well site as a target location, wherein the plurality of rock cores are cored and collected from the plurality of geographical locations in the subterranean formation, and wherein the field operation is performed at the well site as the target location.

* * * * *